United States Patent
Boogaard et al.

(10) Patent No.: US 7,239,922 B1
(45) Date of Patent: Jul. 3, 2007

(54) IMPLANTABLE CABLE HAVING SECURELY ATTACHED RING CONTACTS AND METHOD OF MANUFACTURING THE SAME

(75) Inventors: Jerome J. Boogaard, Forest Grove, OR (US); Robert W. Lucas, Prineville, OR (US); John W. Swanson, Portland, OR (US); Sergey N. Varivoda, Vancouver, WA (US)

(73) Assignee: Advanced Neuromodulation Systems, Inc., Plano, TX (US)

( * ) Notice: Subject to any disclaimer, the term of this patent is extended or adjusted under 35 U.S.C. 154(b) by 337 days.

(21) Appl. No.: 10/700,110

(22) Filed: Nov. 3, 2003

(51) Int. Cl.
*A61N 1/05* (2006.01)
(52) U.S. Cl. .................................................... 607/116
(58) Field of Classification Search ................ 607/36, 607/116; 439/448
See application file for complete search history.

(56) References Cited

U.S. PATENT DOCUMENTS

| | | | |
|---|---|---|---|
| 4,590,950 A * | 5/1986 | Iwaszkiewicz et al. ..... | 607/119 |
| 4,944,088 A * | 7/1990 | Doan et al. ................... | 29/858 |
| 5,016,646 A | 5/1991 | Gotthardt et al. ........... | 128/784 |
| 5,251,643 A * | 10/1993 | Osypka ....................... | 607/122 |
| 5,433,742 A | 7/1995 | Willis ........................... | 607/122 |
| 5,514,172 A * | 5/1996 | Mueller ....................... | 607/122 |
| 5,524,338 A | 6/1996 | Martyniuk et al. ........... | 29/825 |
| 5,902,329 A | 5/1999 | Hoffmann et al. .......... | 607/121 |
| 5,935,465 A | 8/1999 | Cardineau et al. ..... | 219/121.69 |
| 6,181,971 B1 * | 1/2001 | Doan ........................... | 607/116 |
| 6,256,542 B1 | 7/2001 | Marshall et al. ............ | 607/126 |
| 6,493,590 B1 | 12/2002 | Wessman et al. ............ | 607/116 |
| 6,505,401 B1 * | 1/2003 | Doan ........................... | 29/860 |
| 6,952,616 B2 | 10/2005 | Wessman et al. | |
| 7,039,470 B1 | 5/2006 | Wessman | |
| 2004/0093053 A1 | 5/2004 | Gerber et al. | |
| 2006/0265037 A1 | 11/2006 | Kuzma | |

\* cited by examiner

*Primary Examiner*—Carl Layno
*Assistant Examiner*—Eric D. Bertram
(74) *Attorney, Agent, or Firm*—Christopher S.L. Crawford

(57) ABSTRACT

A method of manufacturing a biological electrical stimulus cable. The method begins with a cable portion having a plurality of first conductive wires set into a length of insulative material. A portion of the insulative material is removed from the surface creating an exposed first wire surface. Then, a second conductive wire is connected to the exposed first wire surface and a preformed conductive ring is threaded onto the cable portion and electrically connected to the second conductive wire.

1 Claim, 2 Drawing Sheets

IMPLANTABLE CABLE HAVING SECURELY ATTACHED RING CONTACTS AND METHOD OF MANUFACTURING THE SAME

BACKGROUND OF THE INVENTION

Cables that are designed to be implanted in a patient, typically for pain management or other neurological stimulation, are generally fitted with a series of ring contacts. A ring contact, which circumscribes the cable, makes contact with the desired locations inside the patient's body, regardless of the orientation of the cable.

The presently used technique for attaching the ring connectors is somewhat cumbersome. Typically, each individual wire is stripped and a ring fixture is crimped onto it. This operation requires a fair amount of manual labor, requiring fine coordination, and is, therefore, quite expensive.

SUMMARY

In a first separate aspect the present invention is a method of manufacturing a biological electrical stimulus cable. The method begins with a cable portion having a plurality of first conductive wires set into a length of insulative material. A portion of the insulative material is removed from the surface creating an exposed first wire surface. Then, a second conductive wire is connected to the exposed first wire surface and a conductive ring is placed about the cable portion and electrically connected to the second conductive wire.

In a second separate aspect the present invention is a biological electrical stimulus cable assembly. A cable portion includes a plurality of first conductive wires set into a length of insulative material having a surface. An aperture is defined through the insulative material from the surface of the length of insulative material to one of the conductive wires, thereby creating an exposed first wire surface. A second conductive wire is electrically connected to the exposed first wire surface and a conductive ring that is placed about the cable portion is electrically connected to the second conductive wire.

The foregoing and other objectives, features and advantages of the invention will be more readily understood upon consideration of the following detailed description of the invention, taken in conjunction with the accompanying drawings.

DETAILED DESCRIPTION OF THE PREFERRED EMBODIMENT

Figure 1:
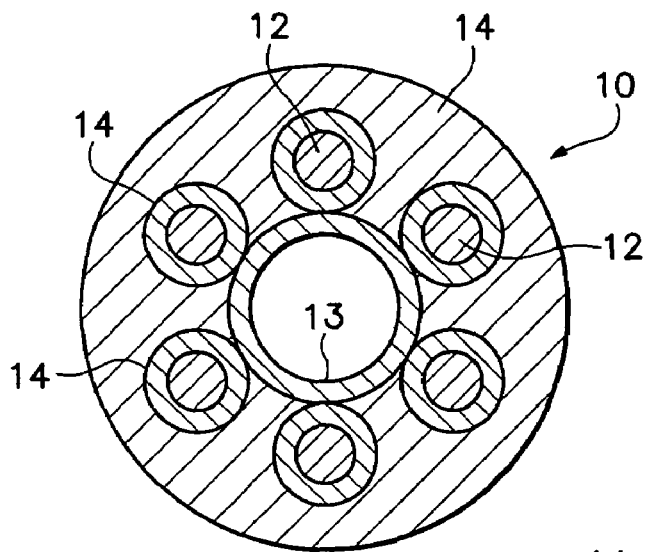
FIG. 1 is a cross-sectional view of a set of wires held within an insulative material, according to a first step in the method of the present invention.
Figure 2:
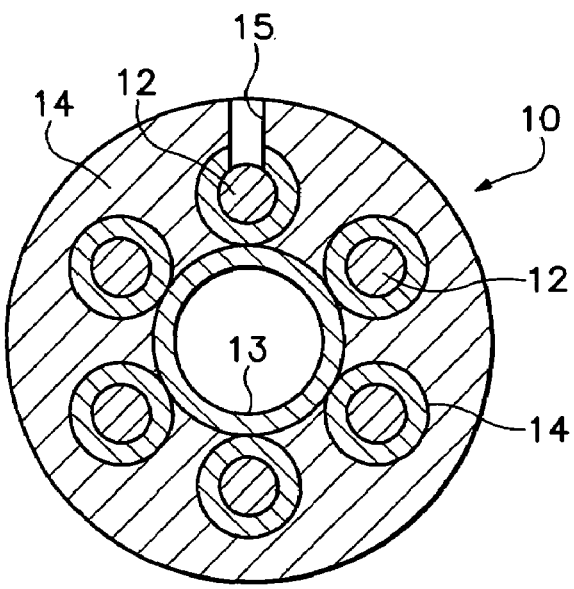
FIG. 2 is a cross-sectional view of the structure of FIG. 1, after a further step in the method of the present invention
Figure 3:
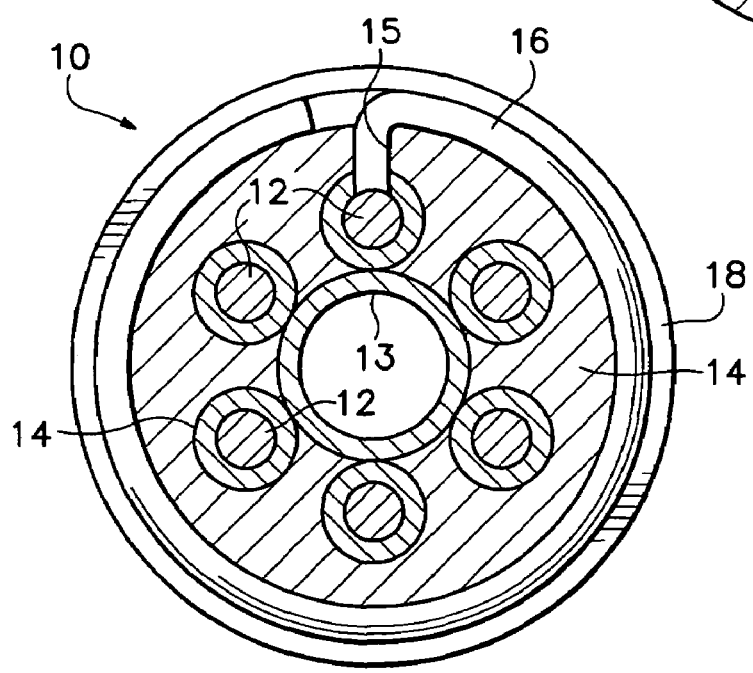
FIG. 3 is a cross-sectional view of the structure of FIG. 1 after another further step in the method of the present invention.

Referring to FIGS. 1–3, a preferred method of practicing the present invention begins with a cable portion 10 having a set of first conductive wires 12 set into a double layered structure of insulative material 14 about a tube 13. In an alternative preferred embodiment a wire is placed in the center of cable portion 10 to impart longitudinal strength to cable portion 10.

Figure 4:
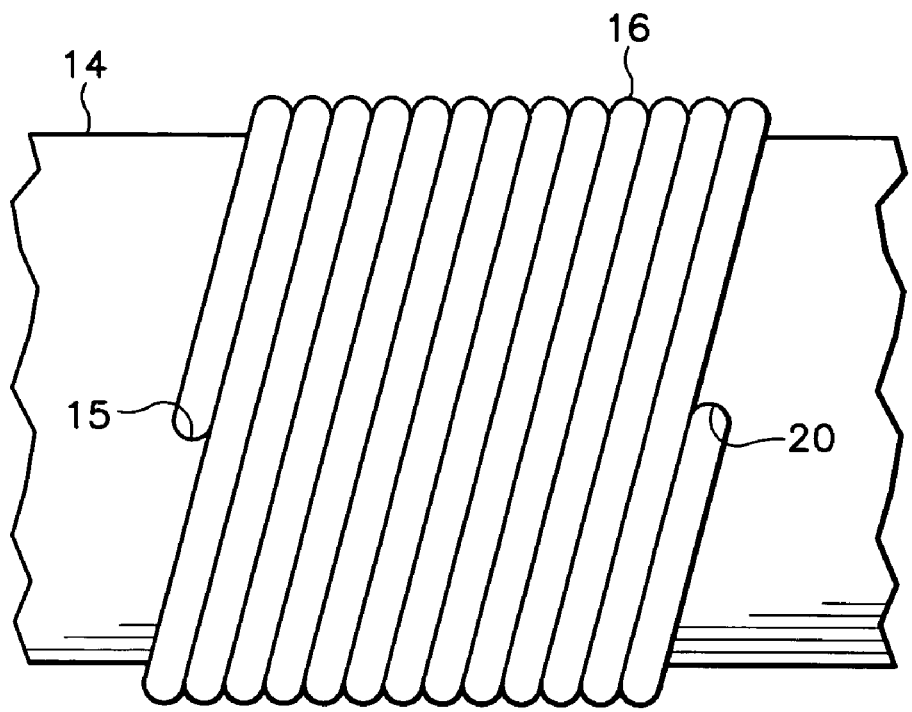
FIG. 4 is a perspective view of the structure of FIG. 1, showing a wire connected in two places.
Figure 5:
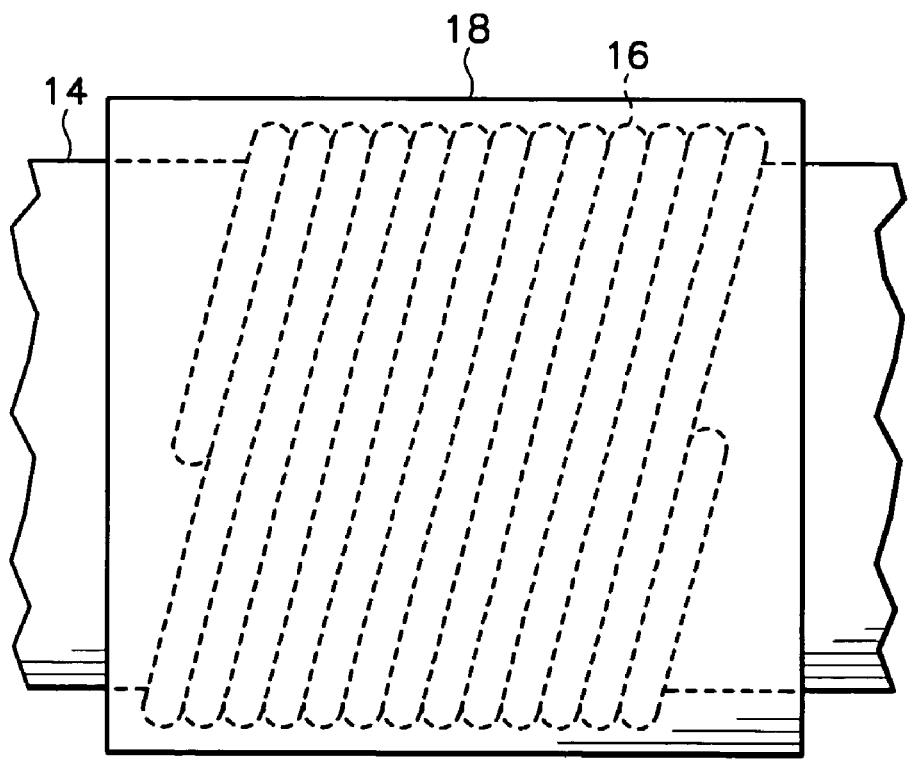
FIG. 5 is a perspective view of a finished product constructed according to the steps of FIGS. 1, 2 and 3.

A laser is used to ablate an aperture 15 (FIG. 2) through insulative material 14 and a second conductive wire 16 is threaded through this aperture 15 into contact with a first conductive wire 12, to which it is laser welded or otherwise attached. A drop of epoxy may then be added into aperture 15, to better secure wire 16. Wire 16 is then wrapped about cable portion 10 and welded to a conductive ring 18 (FIG. 3) that has been placed about cable portion 10. The result is a connection between first conductive wire 12 and conductive ring 18 that is both electrically and structurally robust. In a particular preferred embodiment, shown in FIG. 4, an additional aperture 20 is formed through insulative material 14, spaced apart longitudinally from aperture 15. Wire 16 is then attached to wire 12 by way of aperture 15, wound about cable portion 10 and then attached again to wire 12 through aperture 20. This provides a particularly robust attachment for wire 16 and provides a good amount of surface area to form an excellent electrical connection with ring 18, which is threaded directly radially over wire 16. In an alternative preferred embodiment, wire 16 is wrapped about cable portion 10 a single time only, as it stretches from aperture 15 to aperture 20. In another alternative embodiment wire 16 forms a circumscribing electrode on its own, without the presence of a ring 18 (i.e. FIG. 4 shows the final product.)

In an alternative preferred embodiment a conductive ring 18 is constructed of conductive material directly on the cable portion 10. In an additional alternative preferred embodiment, a partial ring, for example one that extends through three-quarters of a circle is used. In one preferred embodiment cable portion 10 has a diameter of 500 microns, wires 12 are 100 microns thick, wire 16 is 75 microns thick and ring 18 is 50 microns thick and 3,000 microns wide.

Although a frequency multiplied ND:YAG laser is the preferred device for removing insulative material 14, the pulse lengths available from this type of laser are typically not lengthy enough to facilitate laser welding. As a result, for the welding portion of the above described task, the preferred tool is an ND:YAG laser that is not frequency multiplied or a $CO_2$ laser.

To help hold each ring 18 in place, the cable portion 10 may be over molded after the rings 18 have been attached. In this operation the cable portion 10 is encased in a polymer resin, which does not cover the outer surfaces of rings 18. In this manner rings 18 may be affirmatively retained and not permitted to slide longitudinally.

In some embodiments, ring 18 is placed radially over wire 16, while in a different preferred embodiment, wire 16 abuts ring 18 longitudinally.

The terms and expressions which have been employed in the foregoing specification are used as terms of description and not of limitation, and there is no intention, in the use of such terms and expressions, of excluding equivalents of the features shown and described or portions thereof, it being recognized that the scope of the invention is defined and limited only by the claims which follow.

The invention claimed is:

1. A method of manufacturing a biological electrical stimulus cable assembly, comprising:
   a) providing a cable portion, including a plurality of first conductive wires set into a length of insulative material having a surface, wherein the plurality of conductive wires are disposed at substantially the same radial depth within the insulative material, wherein the wires are encapsulated within the insulative material that forms a body of the cable portion;
   b) removing a portion of said insulative material from said surface of said length of insulative material to only a first one of said first conductive wires at a first location, thereby creating a first exposed first wire surface and removing a portion of said insulative material from said surface of said length of insulative material, also only to said first one of said first conductive wires at a second location, thereby creating a second exposed first wire surface, wherein the removing is performed on the cable portion after the first conductive wires have been set within the insulative material of the body of the cable portion;
   c) electrically connecting a second conductive wire to said first exposed first wire surface; and
   d) wrapping said second conductive wire about said cable portion and connecting it to said second exposed first wire surface, thereby creating a circumscribing electrode, wherein the second conductive wire is welded to the first one of said first conductive wires at the second exposed first wire surface.

* * * * *